United States Patent
Yoshikawa et al.

(10) Patent No.: US 9,848,614 B2
(45) Date of Patent: Dec. 26, 2017

(54) METHOD FOR PRODUCING LACTASE-CONTAINING COMPOSITION

(71) Applicant: GODO SHUSEI CO., LTD., Chuo-ku (JP)

(72) Inventors: Jun Yoshikawa, Matsudo (JP); Kazuma Shiota, Matsudo (JP)

(73) Assignee: GODO SHUSEI CO., LTD., Chuo-ku (JP)

( * ) Notice: Subject to any disclaimer, the term of this patent is extended or adjusted under 35 U.S.C. 154(b) by 9 days.

(21) Appl. No.: 14/890,547

(22) PCT Filed: May 12, 2014

(86) PCT No.: PCT/JP2014/062552
§ 371 (c)(1),
(2) Date: Nov. 11, 2015

(87) PCT Pub. No.: WO2014/185364
PCT Pub. Date: Nov. 20, 2014

(65) Prior Publication Data
US 2016/0081361 A1   Mar. 24, 2016

(30) Foreign Application Priority Data
May 13, 2013 (JP) .................................. 2013-101077

(51) Int. Cl.
*A23C 9/12* (2006.01)
*C12N 9/38* (2006.01)
*C12N 9/24* (2006.01)

(52) U.S. Cl.
CPC .......... *A23C 9/1206* (2013.01); *C12N 9/2402* (2013.01); *C12N 9/2468* (2013.01); *C12Y 302/01108* (2013.01); *A23V 2002/00* (2013.01)

(58) Field of Classification Search
CPC ... A23C 9/1206; C12N 9/2468; C12N 9/2402
USPC .......................................................... 426/42
See application file for complete search history.

(56) References Cited

U.S. PATENT DOCUMENTS

| 4,237,230 A * | 12/1980 | Iida ..................... A23C 9/1206 435/207 |
| 2004/0121041 A1 | 6/2004 | Van Beckhoven et al. |
| 2008/0286412 A1* | 11/2008 | Dekker ................ A23C 9/1206 426/42 |
| 2011/0212221 A1 | 9/2011 | Beckhoven et al. |

FOREIGN PATENT DOCUMENTS

| EP | 2 687 598 A1 | 1/2014 |
| JP | 51-76459 | * 7/1976 |
| JP | 2004-534527 A | 11/2004 |
| WO | 2007/060247 A2 | 5/2007 |
| WO | 2011/033633 A1 | 3/2011 |

OTHER PUBLICATIONS

Extended European Search Report dated Nov. 9, 2016 in Patent Application No. 14798365.4.
Alafuele Mbuyi-Kalala et al., "Separation and Characterization of Four Enzyme Forms of β-galactosidase from *Saccharomyces lactis*", European Journal of Biochemistry 178(2), XP55022811, Dec. 1, 1988, pp. 437-443.
Maria V. Flores, et al., "The Proteolytic System of the Yeast *Kluyveromyces lactis*", Yeast, vol. 15, pp. 1437-1448, (1999).
International Search Report and Written Opinion of the International Searching Authority dated Aug. 12, 2014 in PCT/JP14/062552 Filed May 12, 2014.
O. Tossavainen, et al., "Proteolytic changes in lactose hydrolysed UHT milks during storage", Milchwissenschaft, vol. 62, No. 2, Total 6 Pages, (2007).
Maria V. Flores, et al., "The Proteolytic System of the Yeast *Kluyveromyces lactis*", Yeast, vol. 15, pp. 1437-1448, (1999).
International Search Report and Written Opinion of the International Searching Authority Issued Aug. 12, 2014 in PCT/JP14/062552 Filed May 12, 2014.

* cited by examiner

Primary Examiner — Hamid R Badr
(74) Attorney, Agent, or Firm — Oblon, McClelland, Maier & Neustadt, L.L.P.

(57) ABSTRACT

A method for producing a lactase-containing composition which is purified by selectively removing protease contaminating the lactase using simple and easy means; a lactase-containing composition; and a dairy product containing the lactase-containing composition.

A method for producing a lactase-containing composition having a reduced protease content includes: dissolving a composition containing lactase and protease in an aqueous salt solution having an electric conductivity of from 2 to 45 mS/cm; bringing the resultant solution into contact with an ion exchange resin; and collecting a fraction which is not adsorbed onto the ion exchange resin.

13 Claims, 1 Drawing Sheet

[Figure 1]
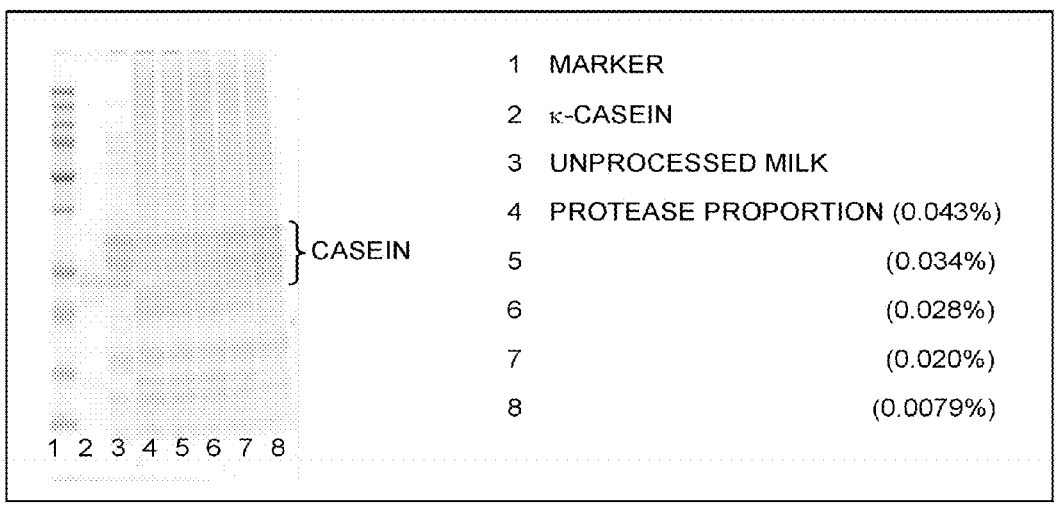
1 MARKER
2 κ-CASEIN
3 UNPROCESSED MILK
4 PROTEASE PROPORTION (0.043%)
5 (0.034%)
6 (0.028%)
7 (0.020%)
8 (0.0079%)
[Figure 2]
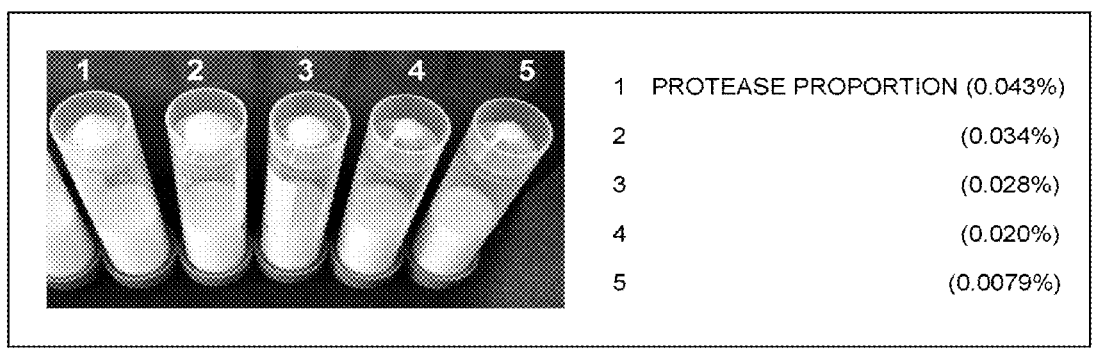
1 PROTEASE PROPORTION (0.043%)
2 (0.034%)
3 (0.028%)
4 (0.020%)
5 (0.0079%)

METHOD FOR PRODUCING LACTASE-CONTAINING COMPOSITION

TECHNICAL FIELD

The present invention relates to a method for producing a lactase-containing composition having a reduced protease content.

BACKGROUND ART

Lactase is an enzyme decomposes lactose into glucose and galactose. While lactose is present in a dairy product using milk beverage such as milk, lactase is present in the small intestine of most humans. Therefore, the lactose in the dairy product is decomposed into glucose and galactose in the small intestine. However, there are partly some humans in whom lactase does not act sufficiently, in which case lactose is not sufficiently decomposed and symptoms such as diarrhea and indigestion occur. Lactase is widely used for decomposing lactose in dairy products. Further, lactase is widely used also for improving the degree of sweetness of milk beverage and fermented milk, producing ice cream and milk jam, imparting a caramel color, for example, to coffee milk, and the like.

Such lactase is produced from yeasts, fungi, bacteria, or the like. In particular, lactase is produced by culturing yeasts such as *Kluyveromyces lactis* (*K. lactis*), *Kluyveromyces fragilis* (*K. fragillis*), and *Kluyveromyces marxianus* (*K. marxianus*). However, a lactase-containing composition derived from such a microorganism contains a small amount of proteases. It is known that protease which contaminates lactase decomposes milk protein, increases the off-flavor (unpleasant odor) of milk, and reduces the storage stability (Non Patent Literature 1 and Patent Literature 2).

It is reported that a reduction in the amount of protease which contaminates lactase can be achieved by binding lactase to a chromatographic resin such as an ion exchange resin and thereafter desorbing or eluting only the lactase (Patent Literatures 1 and 2).

CITATION LIST

Patent Literature

[Patent Literature 1] JP-A-2004-534527
[Patent Literature 2] JP-A-2009-517061

Non Patent Literature

[Non Patent Literature 1] Milchwissenschaft, Vol. 62, No. 4, p. 410-414 (2007)
[Non Patent Literature 2] Yeast, Vol. 15, No. 14, p. 1437-1448 (1999)

SUMMARY OF INVENTION

Technical Problem

However, tens of protease genes are detected, for example, according to the genomic information of *K. lactis*. Further, some of them have been confirmed to be active in a fungal extract solution (Non Patent Literature 2). In order to obtain a pure lactase solution, it is necessary to remove a plurality of proteases contained in the fungal extract solution. Each protease has different properties, and therefore it is exceptionally difficult to remove a plurality of proteases by a single purification step. In order to obtain a pure lactase solution, it is conceivable that the plurality of proteases contained in the fungal extract solution are removed one by one through a plurality of purification steps. Therefore, in order to obtain a pure lactase solution, purification through fractionation operation is required, in which the lactase contained in the fungal extract solution is adsorbed by a plurality of column chromatography and the lactase is selectively eluted. However, the operation is cumbersome, and further requires a lot of equipment and days for the purification. Accordingly, the studies by the present inventors concluded that the aforementioned method is unsuitable as an industrial production method. Further, as the number of purification steps increases, the yield of lactase decreases, which is another problem.

It is an object of the present invention to provide a method for producing a lactase-containing composition which is purified by selectively removing protease which contaminates lactase with a simple and easy means.

It is another object of the present invention to provide: a lactase-containing composition which has a reduced protease content and is suitable for containing in a dairy product using milk beverage; and a dairy product containing the lactase-containing composition.

Solution to Problem

As a result of various studies to develop means for removing protease in a lactase-containing composition by a simple and easy process, the present inventors have found that a lactase-containing composition having a reduced protease content can be obtained, without any elution process, by dissolving the lactase composition containing proteases in an aqueous salt solution having a certain electric conductivity and thereafter bringing it into contact with an ion exchange resin, because lactase permeates therethrough and protease is selectively adsorbed thereon, which is totally unexpected. The present inventors have further found that a dairy product containing thus produced lactase-containing composition eliminates the occurrence of off-flavor and has good tongue texture and good storage stability, as well as the lactase in the dairy product is decomposed.

That is, the present invention provides the following [1] to [7].

[1] A method for producing a lactase-containing composition having a reduced protease content, including: dissolving a composition containing lactase and protease in an aqueous salt solution having an electric conductivity of from 2 to 45 mS/cm; bringing the resultant solution into contact with an ion exchange resin; and collecting a fraction which is not adsorbed onto the ion exchange resin.

[2] The production method according to [1], wherein the composition containing lactase and protease is a lactase-containing composition produced by a microorganism.

[3] The production method according to [1] or [2], wherein the aqueous salt solution is an aqueous solution of an inorganic acid salt.

[4] The production method according to any one of [1] to [3], wherein the ion exchange resin is an anion exchange resin.

[5] The production method according to any one of [1] to [4], wherein the ion exchange resin is an anion exchange resin membrane.

[6] The production method according to any one of [1] to [5], wherein the lactase-containing composition to be obtained has a ratio of protease activity to lactase activity (protease/lactase) of not more than 0.02%.

[7] A lactase-containing composition having a ratio of protease activity to lactase activity (protease activity÷lactase activity×100) of not more than 0.02%.

[8] The lactase-containing composition according to [7], the composition being obtained by the method according to any one of [1] to [5].

[9] The lactase-containing composition according to [7] or [8], wherein for a processed milk obtained by allowing milk to contain 0.1 mass % of the lactase-containing composition and to stand still at 30° C. for 3 months, when the processed milk is centrifuged at 20,000 g for 10 minutes, a value obtained by dividing a mass of the precipitate by a weight of the processed milk is not more than 12%.

[10] A dairy product containing the lactase-containing composition according to any one of [7] to [9].

Advantageous Effects of Invention

According to the present invention, a lactase-containing composition with a reduced amount of protease can be efficiently obtained only by dissolving a lactase composition containing protease in an aqueous salt solution and bringing it into contact with an ion exchange resin.

Further, the lactase-containing composition obtained by the present invention has a ratio of protease activity to lactase activity of not more than 0.02%, which means that the protease activity is significantly reduced, and has totally unexpected effects that milk protein is not decomposed, precipitation is less likely to occur even when the lactase-containing composition is added to milk and stored for a long time, the occurrence of off-flavor of milk beverage is eliminated, and tongue texture of the dairy product to be obtained is improved.

BRIEF DESCRIPTION OF DRAWINGS

FIG. 1 shows results of SDS-PAGE of milk treated with lactase-containing compositions containing protease in various proportions.

FIG. 2 shows curd of the milk treated with the lactase-containing compositions containing protease in various proportions (placed upside down after static storage).

DESCRIPTION OF EMBODIMENTS

A method for producing a lactase-containing composition having a reduced protease content of the present invention includes: (1) a step of dissolving a composition containing lactase and protease in an aqueous salt solution having an electric conductivity of from 2 to 45 mS/cm; and (2) a step of bringing the resultant solution into contact with an ion exchange resin and collecting a fraction which is not adsorbed onto the ion exchange resin.

As the composition containing lactase and protease to be used in step (1) (hereinafter, simply referred to as a raw material lactase-containing composition), a lactase-containing composition obtained by culturing a microorganism which produces lactase can be mentioned. Examples of the microorganism which produces lactase include microorganisms belonging to the genus *Kluyveromyces* (*Kluyveromyces*), the genus *Aspergillus* (*Aspergillus*), and the genus *Bacillus* (*Bacillus*). Among these, microorganisms belonging to the genus *Kluyveromyces* are more preferable. Among the microorganisms belonging to the genus *Kluyveromyces*, *Kluyveromyces fragilis* (*K. fragillis*), *Kluyveromyces lactis* (*K. lactis*), and *Kluyveromyces marxianus* (*K. marxianus*) are preferable, and *Kluyveromyces lactis* is more preferable.

It is preferable that the microorganism which produces lactase be cultured, for example, in a culture medium containing lactose or a nitrogen source under conditions of pH 3 to 10, from 20 to 40° C. and for 24 to 180 hours. In order to collect a raw material lactase-containing composition from the resultant culture, the composition may be extracted, for example, from collected cells, or mutant cells or the like which are released the composition into the extracellular may be used. In the case of culture in a liquid medium, the culture liquid itself may be used.

The raw material lactase-containing composition may be a liquid material including a culture liquid, or may be a solid material obtained by removing moisture from a culture liquid. In the case of removing moisture from the raw material lactase-containing composition, lactase contained in the raw material lactase-containing composition may possibly be inactivated, removal of moisture requires cost, and redissolution of the resultant solid material in an aqueous salt solution as described below, is difficult. Therefore, the raw material lactase-containing composition is preferably a liquid material.

It is preferable that the lactase used in the present invention have an optimum pH for its activity in the neutral region and properties of being inactivated in the acidic region, and the lactase be capable of decomposing lactose in its active state. It is more preferable that the optimum pH for the lactase activity be from 6.0 to 7.5, and the pH at which the lactase is inactivated be from 4.0 to 6.0.

The lactase used in the present invention is not substantially adsorbed onto an anion exchange resin in the presence of a specific aqueous salt solution, which will be described below. Not being substantially adsorbed means that the yield of lactase is 80% or more, preferably 85% or more, and more preferably 90% or more. Since a higher yield of lactase is more preferable, the upper limit is not specifically limited, but the upper limit is, for example, 100%. The yield of lactase herein means a value obtained by dividing the total lactase activity after the ion exchange resin process by the total lactase activity before the ion exchange resin process (with addition of the aqueous salt solution) and multiplying the result by 100.

The raw material lactase-containing composition obtained by culturing the microorganism which produces lactase contains about 0.043% of protease in terms of activity ratio (protease activity÷lactase activity×100; which may be hereinafter referred to as "protease proportion"), even in the case of employing common industrial purification means such as ultrafiltration. Here, the reason why it is expressed in terms of the protease proportion is that, while it is difficult to determine individual values of protease activity and lactase activity uniformly since those values vary depending on the amount of solvent, the values can be expressed in terms of the protease proportion, regardless of the amount of solvent contained in the raw material lactase-containing composition.

The protease contained in the raw material lactase-containing composition means protease detected by a method for measuring protease activity, which will be described below. That is, it means total protease, and does not mean specific protease. The protease has properties of decomposing peptides and proteins in its active state.

The protease contained in the raw material lactase-containing composition has properties of easily adsorbing onto an anion exchange resin, particularly onto a weakly basic anion exchange resin, in the presence of a specific aqueous salt solution, which will be described below. Accordingly, once the protease dissolved in the later-described specific aqueous salt solution is adsorbed onto an anion exchange resin, the protease maintains the adsorbed state on the anion exchange resin.

It is important for the solution used for dissolving the raw material lactase-containing composition to be an aqueous salt solution having an electric conductivity of from 2 to 45 mS/cm, in order to allow the protease in the raw material lactase-containing composition to adsorb selectively onto the ion exchange resin. That is, the lactase contained in the solution permeates through the ion exchange resin without adsorbing thereon, or is liberated after adsorbing onto the ion exchange resin. The electric conductivity is preferably from 10 to 45 mS/cm, more preferably from 18 to 42 mS/cm, further preferably from 20 to 41 mS/cm, and furthermore preferably from 25 to 36 mS/cm.

The means for dissolving the raw material lactase-containing composition in the aqueous salt solution varies depending on whether the raw material lactase-containing composition is liquid or solid at room temperature (25° C.)

When the raw material lactase-containing composition is liquid, with respect to 100 parts by mass of the raw material lactase-containing composition which is a liquid material, 10 parts by mass to 9,900 parts by mass of the aqueous salt solution may be added. Preferably, the amount to be added is 100 parts by mass to 9,900 parts by mass. When a small amount of the aqueous salt solution is added, it is difficult to obtain the electric conductivity within a preferable range, and therefore it is difficult to obtain the effects of the present invention. When a large amount of the salt aqueous solution is added, there is a problem that the process takes more time and becomes cumbersome.

When the raw material lactase-containing composition is solid, with respect to 100 parts by mass of the raw material lactase-containing composition which is a solid material, 10 parts by mass to 9,900 parts by mass of the aqueous salt solution may be added. Preferably, the amount to be added is 100 parts by mass to 9,900 parts by mass. When a small amount of the aqueous salt solution is added, it is difficult to obtain the electric conductivity within the preferable range, and therefore it is difficult to obtain the effects of the present invention. When a large amount of the aqueous salt solution is added, there is a problem that the process takes more time and becomes cumbersome. When the raw material lactase-containing composition is solid, it is preferable that the lactase-containing composition be dissolved or dispersed uniformly by adding the aqueous salt solution.

Examples of the salt contained in the aqueous salt solution having an electric conductivity of from 2 to 45 mS/cm include organic acid salts and inorganic acid salts. However, use of inorganic acid salts is preferable for selective adsorption of protease onto the ion exchange resin and ease of collecting the lactase-containing composition as a target. Examples of the organic acid salts include metal salts and amine salts of organic acids with a molecular weight of 70 to 300 such as acetate, citrate, malate, oxalate, and tartrate. Examples of the inorganic acid salts include metal salts and amine salts of acids such as hydrochloric acid, nitric acid, sulfuric acid, hydrofluoric acid, carbonic acid, boric acid, and phosphoric acid. Among these, the metal salts of inorganic acids are particularly preferable. Examples of the metals herein include alkali metal and alkaline earth metal. The salts may be used individually, or a plurality of types may be mixed for use.

In order to obtain the aqueous solution having an electric conductivity of from 2 to 45 mS/cm using such an organic acid salt or inorganic acid salt, an aqueous solution of an inorganic acid salt is specifically adjusted preferably to from 0.02 to 0.42 M, more preferably to from 0.15 to 0.37 M, and further preferably to from 0.2 to 0.32 M.

The lactase activity in the aqueous salt solution is preferably from 100 to 250,000 U/mL, more preferably from 500 to 120,000 U/mL, and further more preferably from 2,500 to 60,000 U/mL, for selective adsorption of protease onto the ion exchange resin.

Step (2) is a step of bringing the resultant solution into contact with the ion exchange resin and collecting a fraction which is not adsorbed on the ion exchange resin.

Examples of the ion exchange resin include cation exchange resins and anion exchange resins. Examples of the cation exchange resins include strongly acidic cation exchange resins (containing a sulfonic acid group) and weakly acidic cation exchange resins (containing a carboxyl group and a phenolic hydroxy group). Examples of the anion exchange resins include strongly basic anion exchange resins (containing a quaternary ammonium group) and weakly basic anion exchange resins (containing a primary to tertiary amino group). Among these, the anion exchange resins are preferable, and the weakly basic anion exchange resins are more preferable, in view of properties of selectively adsorbing protease.

Further, as a matrix of the ion exchange resin, matrices such as styrene-divinyl benzene, acrylic acid, cellulose, agarose, dextrin, dextran, polysulfone, polyacrylonitrile, and polyethylene can be mentioned. Examples of the form of the ion exchange resin include a powder form, a spherical form, a fibrous form, and a membrane form. Because of the ease of use, the ion exchange resin is preferably in a spherical form or a membrane form so as to be able to be filled into columns. The ion exchange resin is particularly preferably in a membrane form in that the process can be operated in a short time because the process can be performed more conveniently at a higher flow rate. Examples of commercially available products of the ion exchange resin include: DIAION SA Series (strongly basic gel type such as SA10A, 11A, 12A, 20A, and 21A, manufactured by Mitsubishi Chemical Corporation), PA Series (strongly basic porous type such as PA306, 308, 312, 316, 318, 406, 408, 412, 416, and 418, manufactured by Mitsubishi Chemical Corporation), and WA Series (weakly basic acrylic type such as WA10 and 11, and strongly basic highly porous type such as WA20, 21, and 30, manufactured by Mitsubishi Chemical Corporation); Amberlite IRA Series (such as IRA-400, 410, 900, and 93ZU, manufactured by Mitsubishi Chemical Corporation); Mustang Q Series (strongly basic ion exchange membrane, manufactured by Pall Corporation); and QyuSpeed D Series (weakly basic ion exchange membrane, manufactured by Asahi Kasei Corporation).

The means for bringing the solution into contact with the ion exchange resin varies depending on the form of the ion exchange resin. Examples thereof include a batch process in which, after the adsorption by adding the ion exchange resin to the solution and stirring the solution, the ion exchange resin is removed by filtering operation; a column process in which the adsorption process is performed by passing the solution through a column filled with the ion exchange resin; and a membrane process in which the adsorption process is performed by passing the solution through an ion exchange resin membrane. Among these, the column process and the membrane process are more preferable.

In the case of the column process or membrane process, the passing rate of the solution is preferably SV (space velocity)=from 0.1 to 100 [m$^{-1}$], more preferably from 1 to 13 [m$^{-1}$].

When the solution is brought into contact with the ion exchange resin and is passed therethrough, the protease in the solution is selectively adsorbed onto the ion exchange resin. Therefore, a lactase-containing composition having a reduced protease content can be obtained by collecting the passing liquid through the column or membrane (fraction which is not adsorbed onto the ion exchange resin).

Here, "having a reduced protease content" means that the protease activity is reduced as compared to that before the process. Accordingly, the ratio of protease activity to lactase activity (protease activity÷lactase activity×100) of the lactase-containing composition to be obtained is preferably not more than 0.020%, further preferably not more than 0.015%, particularly preferably not more than 0.010%. Since a lower protease proportion is more preferable, the lower limit is not specifically limited. The lower limit is, for example, 0 (where no protease activity is detected).

The activity of lactase contained in the passing liquid obtained by the aforementioned process is preferably from 100 to 250,000 U/mL, more preferably from 500 to 120,000 U/mL, and further more preferably 2,500 to 60,000 U/mL.

The activity of protease contained in the passing liquid obtained by the aforementioned process is preferably not more than 100 U/mL, more preferably not more than 50 U/mL, further preferably not more than 25 U/mL. Since a lower activity of protease is more preferable, the lower limit is not specifically limited. The lower limit is, for example, 0.

The passing liquid obtained by the aforementioned process may be further purified, for example, by ammonium sulfate fractionation, affinity chromatography, and hydrophobic chromatography, and may be powderized by freeze drying or spray drying, as needed.

The step (1) and step (2) of the present invention are preferably performed under conditions in which the lactase activity is not lost, such as the conditions of from 1 to 30° C.

The lactase-containing composition to be obtained by the present invention has a reduced protease content as described above, in which the ratio of protease activity to lactase activity is preferably not more than 0.020%, more preferably not more than 0.015%, further preferably 0.010%.

The lactase-containing composition of the present invention has an exceptionally reduced protease activity, and therefore exerts totally unexpected effects that milk protein is not decomposed even when milk is added to the lactase composition, precipitation is less likely to occur even when the lactase-containing composition is added to milk and stored for a long time, the occurrence of off-flavor of milk beverage is eliminated, and tongue texture of the dairy product to be obtained is improved. Here, the effect of improving the tongue texture is totally heterogeneous from the effect of reducing the off-flavor, and it is quite different also from the effects of sweetness, bitterness, and the like. Further, the effect of suppressing the occurrence of precipitation can be specifically confirmed by the fact that for a processed milk obtained by allowing milk to contain 0.1 mass % of the lactase-containing composition and to stand still at 30° C. for 3 months, when the processed milk is centrifuged at 20,000 g for 10 minutes to obtain a precipitate, a value obtained by dividing a mass of the precipitate by a weight of the processed milk is not more than 12%.

Accordingly, the lactase-containing composition of the present invention can be widely used for various dairy products. Here, examples of the dairy products include milk beverage such as milk, fermented milk, ice cream, and milk jam.

The "milk beverage" serves as a raw material of fermented milk such as yogurt. The milk beverage includes both milk beverage before sterilization and milk beverage after sterilization. The lactase-containing composition can be added before sterilization or after sterilization in accordance with laws and regulations. As specific raw materials of the milk beverage, water, raw milk, sterilized milk, nonfat milk, whole milk powder, skimmed milk powder, buttermilk, butter, cream, whey protein concentrate (WPC), whey protein isolate (WPI), α (alpha)-La, and β (beta)-Lg can be mentioned. A gelatin which has been warmed in advance, for example, may be appropriately added. The raw material milk is publicly known, and may be prepared using a known method. The raw material of the milk beverage in the present invention preferably contains milk. A raw material consisting of milk at 100% may be used as the raw material of the milk beverage.

The "fermented milk" may be any of "fermented milk", "lactic acid bacteria beverage of dairy product", and "lactic acid bacteria beverage" which are defined by the ministerial ordinance, such as yogurt and milk. Generally, plain yogurt is produced by filling a container with a raw material, and thereafter fermenting it (post-fermentation). Meanwhile, soft yogurt and yogurt drink are produced by subjecting fermented milk after fermentation to an atomization process or a homogenization process, and thereafter filling a container with the fermented milk (pre-fermentation). The lactase-containing composition of the present invention can be used for both post-fermentation and pre-fermentation. The raw material of fermented milk preferably contains milk. A raw material consisting of 100% milk may be used as the raw material of the fermented milk.

The amount of the lactase-containing composition to be contained in the dairy product varies depending on the type of the dairy product. It is sufficient that the proportion of protease contained in the dairy product is not more than 0.02%.

The dairy product using the present invention is preferably applied to a dairy product containing the lactase contained in the lactase-containing composition as it is in the active state without the loss of activity (such as long-life milk), for example. The reason for this is that, since protease is contained in the lactase-containing composition, the protease is allowed to act more easily as the storage life of the long-life milk increases, in which case the off-flavor tends to occur.

EXAMPLES

Next, the present invention will be described further in detail by way of examples. However, the present invention is not limited to these examples.

(Method for Measuring Lactase Activity)

0.5 mL of a diluted enzyme sample was taken in a test tube, and 0.5 mL of a 100 mM KH$_2$PO$_4$—NaOH buffer solution (pH 6.5) to which manganese chloride was added to be 0.1 mM was added thereto and the mixture was stirred. Thereafter, the mixture was kept warm at 37° C. for 3 minutes. 1.0 mL of a 0.1% ortho-nitrophenyl-β-galactoside (ONPG) solution which had been kept warm in advance at 37° C. was added thereto and the mixture was rapidly stirred, and the mixture was kept warm accurately at 37° C. for 1 minute. 2.0 mL of a 0.2 M sodium carbonate solution was added thereto and the mixture was rapidly stirred, so that the reaction was stopped. As a blank, 0.5 mL of a diluted enzyme sample was taken in a test tube, and 0.5 mL of the aforementioned buffer solution was added thereto and the mixture was stirred. Thereafter, 2.0 mL of a reaction stop solution was added thereto, which was kept warm at 37° C. for 3 minutes. 0.1 mL of an ONPG solution which had been kept warm in advance at 37° C. was added thereto and the mixture was stirred, and the mixture was kept warm accurately at 37° C. for 1 minute. Using distilled water as a control, the absorbance at 420 nm of each reaction solution was measured, and a value obtained by subtracting the absorbance of the blank therefrom was defined as a measured value. One unit of the lactase activity was defined as the amount of enzyme required to change the measured value by one per 10 minutes.

(Method for Measuring Protease Activity)

0.5 mL of a diluted enzyme sample was taken in a test tube, which was kept warm at 30° C. for 3 minutes. 2.5 mL of a substrate solution (a 0.6% casein solution dissolved in a 100 mM $KH_2PO_4$—NaOH buffer solution (pH 6.5) to which manganese chloride was added to be 0.1 mM) which had been kept warm in advance at 30° C. was added thereto and the mixture was rapidly stirred, and the mixture was accurately kept warm at 30° C. for 60 minutes. 2.5 mL of a reaction stop solution (1.8% trichloroacetic acid, 1.8% anhydrous sodium acetate, and 2% acetic acid) was added thereto and the mixture was rapidly stirred, so that the reaction was stopped. After being left standing in a thermostatic bath for 30 minutes, it was naturally filtered using filter paper (filter paper No. 4A, manufactured by Advantec Toyo Kaisha, Ltd). As a blank, 0.5 mL of a diluted enzyme sample was taken in a test tube, to which was added 2.5 mL of a reaction stop solution. 2.5 mL of a substrate solution was further added thereto and mixed. After the mixture was left standing in a thermostatic bath for 30 minutes, it was spontaneously filtered using filter paper (filter paper No. 4A, manufactured by Advantec Toyo Kaisha, Ltd). Using distilled water as a control, the absorbance at 275 nm of each reaction solution was measured, and a value obtained by subtracting the absorbance of the blank therefrom was defined as a measured value. A standard straight line was determined from tyrosine dissolved to have the same composition of the reaction solution, and the tyrosine concentration of each measured value was determined. One unit of the protease activity was defined as the amount of enzyme required to liberate 1 μg of tyrosine per 10 minutes.

Example 1

(Preparation of Lactase Preparation with Reduced Protease Content Using Weak Anion Exchange Group)

10 mL of GODO-YNL (a lactase preparation [with a lactase activity of 5,000 U/mL and a ratio of protease activity to lactase activity (hereinafter, referred to as protease proportion) of 0.043%], manufactured by GODO SHUSEI CO., LTD diluted 10-fold with a 20 mM $KH_2PO_4$—NaOH buffer solution (pH 6.5 and 25 mS/cm) containing 0.2 M KCl was passed through QyuSpeed D (with a volume of 0.6 mL), manufactured by Asahi Kasei Corporation having a weak anion exchange group which had been conditioned in advance with the same buffer solution. The protease proportion of the lactase preparation after collection was reduced from 0.043% to 0.0084% (Table 1). The yield of lactase herein means a value obtained by dividing total lactase activity after the process by total lactase activity before the process and multiplying the result by 100. The yield of lactase is 80% or more as a minimum required practical level, 85% or more as a less problematic practical level, and preferably 90% or more.

TABLE 1

Protease content reduction in lactase preparation by weak anion exchange process

|  | Lactase yield (%) | Protease proportion (%) | Protease activity (U/mL) |
|---|---|---|---|
| Before processing | — | 0.043 | 2.15 |
| After ion exchange | 90 | 0.0084 | 0.42 |

Example 2

(Preparation of Lactase Preparation with Reduced Protease Using Strong Anion Exchange Group)

10 mL of GODO-YNL (with a lactase activity of 5,000 U/mL and a protease proportion of 0.043%) diluted 10-fold with a 20 mM $KH_2PO_4$—NaOH buffer solution (pH 6.5 and 25 mS/cm) containing 0.2 M KCl was passed through Mustang Q (Acrodisc Unit, manufactured by Pall Corporation, with a pore size of 0.8 μm and a diameter of 25 mm) having a strong anion exchange membrane. Even when a strong ion exchange group was used, the protease proportion after collection was reduced from 0.043% to 0.019% (Table 2).

TABLE 2

Protease content reduction in lactase preparation by strong anion exchange process

|  | Lactase yield (%) | Protease proportion (%) | Protease activity (U/mL) |
|---|---|---|---|
| Before process | — | 0.043 | 2.15 |
| After ion exchange | 98 | 0.019 | 0.95 |

Example 3

(Studies on Electric Conductivity)

10 mL of GODO-YNL (with a lactase activity of 5,000 U/mL and a protease proportion of 0.043%) diluted 10-fold with a 20 mM $KH_2PO_4$—NaOH buffer solution (pH 6.5 and from 2 to 45 mS/cm) containing 0 to 0.4 M KCl was passed in the same manner as in Example 1. The lactase preparation after collection had a yield of lactase of 90% or more with 20 mS/cm (0.2 M) or more, referring to the values shown in Table 1 which are the results of Example 1, since the lactase itself was adsorbed onto the ion exchange group when the electric conductivity was low (less than 20 mS/cm). The protease proportion was significantly reduced from 0.043% as compared to that before the process in all cases (Table 3).

TABLE 3

Influence of electric conductivity on protease content reduction by weak anion exchange process

| | | Lactase yield (%) | Protease proportion (%) | Protease activity (U/mL) |
|---|---|---|---|---|
| Before process | | — | 0.043 | 2.15 |
| After ion exchange | | | | |
| (Electric conductivity) | (KCl concentration) | | | |
| 2 mS/cm | 0M | 30 | 0 | 0 |
| 13 mS/cm | 0.1M | 30 | 0 | 0 |
| 19 mS/cm | 0.15M | 63 | 0.0013 | 0.065 |
| 29 mS/cm | 0.25M | 95 | 0.0079 | 0.395 |
| 36 mS/cm | 0.3M | 93 | 0.015 | 0.75 |
| 41 mS/cm | 0.35M | 90 | 0.026 | 1.30 |
| 45 mS/cm | 0.4M | 91 | 0.028 | 1.40 |

Example 4

(Decomposition of Milk Protein by Lactase-Containing Composition)

A lactase-containing composition was prepared by mixing the sample before the aforementioned ion exchange process with the sample after the aforementioned ion exchange process so as to have a lactase activity of 5,000 U/mL and a protease proportion of 0.0079% to 0.043%. This was added to 30 mL of commercially available milk (whole milk) to be 0.3 mL, which was allowed to stand still at 30° C. for 3 months. Each processed milk 3 months after was subjected to SDS-PAGE. As a result, casein bands were decomposed, as shown in FIG. 1, in accordance with the protease proportion as compared to unprocessed milk. In particular, K-casein was obviously decomposed, whose band was undetected when the protease proportion was 0.028% or more.

Each processed milk after 3 months tended to have reduced off-flavor and improved storage stability as the protease proportion is reduced. The processed milk with a protease proportion of not more than 0.02% was confirmed to be free from problems of off-flavor and storage stability.

Example 5

(Decomposition of Milk Protein Depending on Protease Level)

In the lactase processed milk of Example 4, curds were observed at the bottom of the container which had been allowed to stand still. Precipitation of the curds was significantly reduced when the protease proportion was not more than 0.020%, as shown in FIG. 2. Further, milk treated with a lactase preparation having a protease proportion of not more than 0.020% surprisingly had good tongue texture and good quality of taste. Therefore, it was demonstrated that the protease proportion in the lactase preparation with no influence on milk protein was desirably not more than 0.020%.

Further, part of the processed milk was centrifuged at 20,000 g (15,000 rpm) for 10 minutes, and the percentage of precipitation in the processed milk was investigated. After the centrifugation, a supernatant was separated from a precipitate by decantation, and the wet weight of the precipitate was immediately determined. As a result, the precipitation percentage decreased when the protease proportion was not more than 0.020%. The precipitation percentage herein is a value obtained by dividing the wet weight of precipitate occurring in the lactase processed milk by the weight of the lactase processed milk and multiplying the result by 100.

TABLE 4

Percentage of precipitation occurrence in lactase processed milk with each protease proportion

| Protease proportion (%) | Precipitation percentage (%) |
|---|---|
| 0.043 | 15 |
| 0.034 | 15 |
| 0.028 | 14 |
| 0.020 | 12 |
| 0.0079 | 10 |

By focusing on the protease proportion, a new effect of improving the tongue texture was further found, in addition to reduction of off-flavor and improvement of storage stability. Good tongue texture can be confirmed for the first time upon actual eating, which is therefore a quite different effect from off-flavor which can be determined by odor, and storage stability which can be determined by odor, visual perception, and the like. Accordingly, good tongue texture is recognized as a heterogeneous effect from off-flavor or storage stability also by those skilled in the art.

It is inferred that the tongue texture can be improved because decomposition of casein is prevented by focusing on the protease proportion. Further, decomposition of lactose can prevent deposition of lactose in condensation and at low temperature, and therefore this technique can be applied to condensed milk and ice cream.

Further, since the tongue texture was improved by adjusting the protease proportion to not more than 0.02%, improvement of the skin texture is also expected. Possibilities, for example, for applications to cosmetics containing milk components and applications in the bath or the like by making use of the good skin texture have been suggested.

The invention claimed is:

1. A method for producing a lactase-comprising composition having a reduced protease content, the method comprising:
   dissolving a composition comprising lactase and protease in an aqueous salt solution having an electric conductivity of from 2 to 45 mS/cm to obtain a resultant solution;
   bringing the resultant solution into contact with an ion exchange resin; and
   collecting a fraction which is not adsorbed onto the ion exchange resin.

2. The production method according to claim 1, wherein the composition comprising lactase and protease is a lactase-comprising composition produced by a microorganism.

3. The production method according to claim 1, wherein the aqueous salt solution is an aqueous solution of an inorganic acid salt.

4. The production method according to claim 1, wherein the ion exchange resin is an anion exchange resin.

5. The production method according to claim 1, wherein the ion exchange resin is an anion exchange membrane.

6. The production method according to claim 1, wherein the lactase-comprising composition having a reduced protease content has a ratio of protease activity to lactase activity of not more than 0.02%.

7. The production method according to claim 1, wherein the aqueous salt solution has a concentration of from 0.02 M to 0.42 M.

8. The production method according to claim 1, wherein a lactase activity in the aqueous salt solution is from 100 to 250,000 U/mL.

9. The production method according to claim 1, wherein a lactase activity in the aqueous salt solution is from 2,500 to 60,000 U/mL.

10. The production method according to claim 1, wherein the ion exchange resin is a cation exchange resin comprising a sulfonic acid group or a cation exchange resin comprising a carboxyl group and/or a phenolic hydroxy group.

11. The production method according to claim 1, wherein the ion exchange resin is an anion exchange resins comprising a quaternary ammonium group or an anion exchange resins comprising a primary, secondary or tertiary amino group.

12. The production method according to claim 1, wherein a matrix of the ion exchange resin is selected from the group consisting of styrene-divinyl benzene, acrylic acid, cellulose, agarose, dextrin, dextran, polysulfone, and polyacrylonitrile.

13. The production method according to claim 1, wherein the ion exchange resin is in a form of a column or a membrane and a passing rate of the solution, a space velocity (SV), is from 0.1 to 100 $[m^{-1}]$.

* * * * *